(12) United States Patent  
Shanks et al.

(10) Patent No.: US 9,149,650 B2  
(45) Date of Patent: *Oct. 6, 2015

(54) NON-INVASIVE METHOD FOR SLIMMING A HUMAN BODY USING LASER ENERGY OF WAVELENGTHS SHORTER THAN 632 NM

(71) Applicant: Erchonia Corporation, McKinney, TX (US)

(72) Inventors: Steven C Shanks, McKinney, TX (US); Kevin B Tucek, McKinney, TX (US)

(73) Assignee: Erchonia Corporation, McKinney, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/336,401

(22) Filed: Jul. 21, 2014

(65) Prior Publication Data

US 2014/0343638 A1  Nov. 20, 2014

Related U.S. Application Data

(63) Continuation of application No. 13/785,346, filed on Mar. 5, 2013, now Pat. No. 8,813,756, which is a continuation-in-part of application No. 11/053,369, filed on Feb. 7, 2005, now Pat. No. 8,932,338.

(60) Provisional application No. 60/542,720, filed on Feb. 6, 2004.

(51) Int. Cl.
*A61B 19/00* (2006.01)
*A61N 5/06* (2006.01)
(Continued)

(52) U.S. Cl.
CPC ..... *A61N 5/0613* (2013.01); *A61B 2018/00464* (2013.01); *A61N 2005/067* (2013.01); *A61N 2005/0642* (2013.01); *A61N 2005/0644* (2013.01); *A61N 2005/0651* (2013.01); *A61N 2005/0662* (2013.01)

(58) Field of Classification Search
CPC ............... A61N 2007/0008; A61N 2005/067; A61N 2005/0642; A61N 5/067; A61N 5/0616; A61N 5/0618; A61N 2005/0661; A61B 2018/00452; A61B 18/203; A61B 18/20
USPC ............ 607/8–91, 93, 94; 606/3, 9; 128/898
See application file for complete search history.

(56) References Cited

U.S. PATENT DOCUMENTS 6,354,297 B1 *  3/2002  Eiseman ................. 128/898
6,443,978 B1 *  9/2002  Zharov ................... 607/91
(Continued)

OTHER PUBLICATIONS

Patent Trial and Appeal Board Opinion, Ex Parte Lim, Shanks, Niera, issued Jun. 4, 2014 in U.S. Appl. No. 11/053,369, p. 4, regarding U.S. Pat. No. 6,676,655's disclosure of filtered multichromatic light.

*Primary Examiner* — Ahmed Farah
(74) *Attorney, Agent, or Firm* — Sandra L. Etherton

(57) ABSTRACT

A noninvasive method of slimming a patient's body by applying laser energy having a wavelength shorter than 632 nm externally through the skin of the patient. One or more areas of a patient's body, preferably the more fatty regions, such as the abdominal, buttock, lower back, thigh, bust or arm regions, is measured. Objective measurements are made of body criteria, including external dimension, percentage body fat, fat mass, or body mass. Sufficient laser energy, preferably in a range of 0.03-0.1 J/cm$^2$, is applied to one or more of those areas to cause a reduction in the measurement in the lasered areas, as well as overall body slimming. The preferred embodiments use laser light at about 532 nm, 440 nm, or 405 nm. Preferably 18 mW or 25 mW laser diodes are used to apply laser energy at 0.03-0.1 J/cm$^2$ for 15 minutes, every other day for 1-4 weeks, depending on the amount of slimming desired.

16 Claims, 3 Drawing Sheets

(51) Int. Cl.
   *A61N 5/067*     (2006.01)
   *A61B 18/00*     (2006.01)

(56) References Cited

U.S. PATENT DOCUMENTS

| 6,605,079 | B2 * | 8/2003 | Shanks et al. | 606/2 |
| 6,676,655 | B2 * | 1/2004 | McDaniel | 606/9 |
| 7,101,385 | B2 * | 9/2006 | Shellman | 607/88 |
| 8,813,756 | B1 * | 8/2014 | Shanks et al. | 128/898 |
| 8,932,338 | B2 * | 1/2015 | Lim et al. | 607/89 |
| 9,028,469 | B2 * | 5/2015 | Jones et al. | 606/2 |
| 2008/0262574 | A1 * | 10/2008 | Briefs et al. | 607/88 |
| 2010/0082019 | A1 * | 4/2010 | Neev | 606/9 |
| 2011/0046616 | A1 * | 2/2011 | Manstein | 606/13 |

* cited by examiner

NON-INVASIVE METHOD FOR SLIMMING A HUMAN BODY USING LASER ENERGY OF WAVELENGTHS SHORTER THAN 632 NM

CROSS-REFERENCE TO RELATED APPLICATIONS

This application is a continuation-in-part of co-pending, U.S. patent application Ser. No. 11/053,369 filed Feb. 7, 2005, which claims the benefit of U.S. Provisional Application No. 60/542,720 filed Feb. 6, 2004. This application is a continuation of co-pending U.S. patent application Ser. No. 13/785,346 filed Mar. 5, 2013. application Ser. No. 11/053,369, 60/542,720 and 13/785,346 are incorporated by reference in their entirety.

FIELD OF INVENTION

This invention relates to a method for non-invasive, non-destructive shaping and contouring of a human body by external means. In particular, this invention relates to the application of laser energy with wavelengths shorter than 632 nm to targeted external regions of a patient's body to slim the patient's body.

BACKGROUND

There is a great demand to be slimmer. The tried and true method of taking in fewer calories than a person expends results in weight loss, and the resultant slimming effect occurs over the body as a whole. For more targeted contouring, many people resort to the cosmetic surgical procedure known as liposuction, wherein excess adipose tissue, also known as fat, is suctioned from the body of a patient. The typical purpose of the liposuction procedure is to leave the patient thinner in desired areas, with aesthetically more appealing body contours. For example, liposuction is often performed on patients to remove excess fat in the abdominal, buttock, thigh, breast or arm regions of the body.

Liposuction is performed by inserting a narrow tube, or cannula, through a tiny incision in the skin into the subcutaneous fatty tissue. The cannula is repeatedly pushed then pulled through the fat layer, separating and puncturing the fat cells and suctioning them out. Suction action through the cannula is provided by a vacuum pump or a large syringe. The procedure carries with it some risks and side effects. Due to the physical damage induced, the procedure can damage nerves, lymphatics and vasculature in the surrounding area, often resulting in significant loss of blood as the blood is vacuumed out with the fat and the formation of seroma due to damaged lymphatic channels. In addition, the post-procedure recovery period is long and often accompanied by a great deal of inflammation, bruising and concomitant pain.

Since the liposuction technique was first developed there have been many improvements to techniques for contouring the body, with the goal of making the surgery less dangerous for the patient, reducing the negative aspects of the post-operative recovery period, and making it more commercially viable for the practitioner who treats the patient.

Non-invasive methods of body contouring are preferred over invasive methods to minimize trauma to the patient, reduce the risk of infection, and speed up recovery time, among other reasons. To avoid invasive procedures, electromagnetic energy, such as microwave, ultrasound or radio frequency radiation, has been used to reduce fat. In U.S. Pat. No. 5,507,790 issued to Weiss, a method is described in which a medicament is applied to a patient's skin where fat removal is desired and focused electromagnetic energy is applied to the same work site to heat the fatty tissue and increase fat lipolysis. In U.S. Pat. No. 5,143,063, Fellner takes this method even farther, applying sufficient electromagnetic radiation to destroy the fat cells. Yet another method is to inject an intumescing solution below the skin and apply electromagnetic energy externally to the body. These procedures are disadvantageous in that they utilize such high energy sources that they excessively heat the surrounding tissue, which can result in damage to the tissue and pain. Again, recovery time is significant.

In a recent innovation, a procedure was developed by a group including one of the inventors of this method which uses red LLLT alone, to contour the body by reducing fat. The procedure is described in U.S. Pat Pub. 2005/0203594 and involves using a device having lasers of less than 1 W to apply one or more treatments of 635 nm laser energy externally to the patient to release at least a portion of the intracellular fat into the interstitial space. Upon sufficient doses of this low-level laser energy at 635 nm, the cell membrane was thought to be momentarily disrupted, releasing the intracellular fat into the interstitial space. Upon cessation of the energy application, the pores closed and the cell membrane returned to contiguity. The treated and surrounding tissue was not heated and not damaged, and the patient felt no sensation during the application of the 635 nm laser energy. The released fat was removed from the patient's body through one or more of the patient's normal bodily systems. This method revolutionized the market for body contouring because it reduced fat with no trauma to the patient.

The LLLT industry heretofore believed that using lasers with wavelengths shorter than about 632 nm would fail to non-traumatically shape a patient's body. One reason is that it is believed that the shorter wavelengths would not penetrate the skin deep enough to reach the fat cells and other tissues needed to attain shaping. For example, U.S. Pat. No 7,771,374 issued to Slatkine, discloses that melanin and blood in the skin do not allow light at 405 nm, 514 nm or 585 nm to penetrate deep into the skin due to strong absorption. Instead, the patent discloses using a vacuum to expel blood from the treatment area to improve treatment of the tissue.

Lasers emit electromagnetic energy, which can be described by frequency, wavelength, or energy. Laser diodes with shorter wavelengths have a higher energy than laser diodes with longer wavelengths. Another reason that it was believed that the shorter wavelengths would fail to non-traumatically reduce fat was because in order to penetrate the skin to a deep-enough depth, the higher-energy wavelengths would heat the surrounding tissue through which the laser penetrated, traumatizing the patient. Laser devices emitting wavelengths shorter than about 632 nm lasers are known in the art, but only for ablative treatments. To cool the radiated skin and minimize trauma to the patient, complicated cooling components were invented to reduce the heat generated by the shorter wavelength therapeutic lasers. For example, in U.S. Pat. Pub 2008/0294153, Altshuler describes a cooling system for a green laser light used as a thermal treatment to remove a red portion of a tattoo by causing the death of the cells containing the tattoo ink particles by rupture or apoptosis.

Yet another reason that it was believed that the shorter wavelengths would fail to non-traumatically shape a targeted area of the body is that any wavelength other than about 635 nm would be ineffective for stimulating the cell to open the transitory pore to release fat. Consequently, only devices emitting red laser energy have been used for shaping the body.

While the red LLLT is effective in reducing fat, patients and doctors have clamored for a non-invasive method of slimming that takes less treatment time. It would be desirable to capitalize on the higher energy of shorter wavelengths to do so in less time than prior art methods, without traumatizing the tissue. Therefore, an object of this invention is to provide a non-invasive method of reducing the circumference of desired areas of a human body in less time than prior art methods. Another object is to provide a non-invasive method of reducing the circumference desired areas of a human body in less time than prior art methods, which does not destroy fat cells or otherwise damage surrounding tissue or structures. It is another object of the method to slim the patient's body as a whole. It is another object to provide a non-invasive method of slimming a human body using lasers emitting wavelengths shorter than 632 nm.

SUMMARY OF THE INVENTION

This invention is a noninvasive method of slimming a patient's body by applying laser energy having a wavelength shorter than 632 nm externally through the skin of the patient. One or more areas of a patient's body, preferably the more fatty regions, such as the abdominal, buttock, lower back, thigh, bust or arm regions, is measured. Objective measurements are made of body criteria, including circumference, percentage body fat, fat mass, or body mass. Sufficient laser energy, preferably in a range of 0.03-0.1 J/cm$^2$, is applied to one or more of those areas to cause a reduction in the measurement in the lasered areas, as well as overall body slimming. The preferred embodiments use laser light at about 532 nm, 440 nm, or 405 nm. Preferably 18 mW or 25 mW laser diodes are used to apply laser energy at 0.03-0.1 J/cm$^2$ for 15 minutes, every other day for 1-4 weeks, depending on the amount of slimming desired.

DETAILED DESCRIPTION OF THE INVENTION

Lasers emit electromagnetic energy, which can be described by frequency, wavelength, or energy. Laser diodes with shorter wavelengths have a higher energy than laser diodes with longer wavelengths. See Table 1:

| Wavelength (nm) | Energy (eV) | % difference over 635 nm |
|---|---|---|
| 635 (red) | 1.82 | — |
| 532 (green) | 2.24 | 23% |
| 440 (violet) | 2.84 | 56% |
| 405 (violet) | 3.09 | 68% |

Despite heretofore long-recognized reasons that using wavelengths shorter than 635 nm to treat patients would be ineffective—or worse, dangerous—the present invention is a method for slimming a patient's body non-traumatically by using shorter wavelengths, preferably green or violet laser light. The present invention uses green or violet laser light instead of red laser light with the surprising result of non-traumatically slimming a patient in far less time than red laser light would have taken. In general, using green laser light instead of red laser light decreases the time of treatment by 25% and also results in 25% more fat reduction across the treated area.

Figure 2:
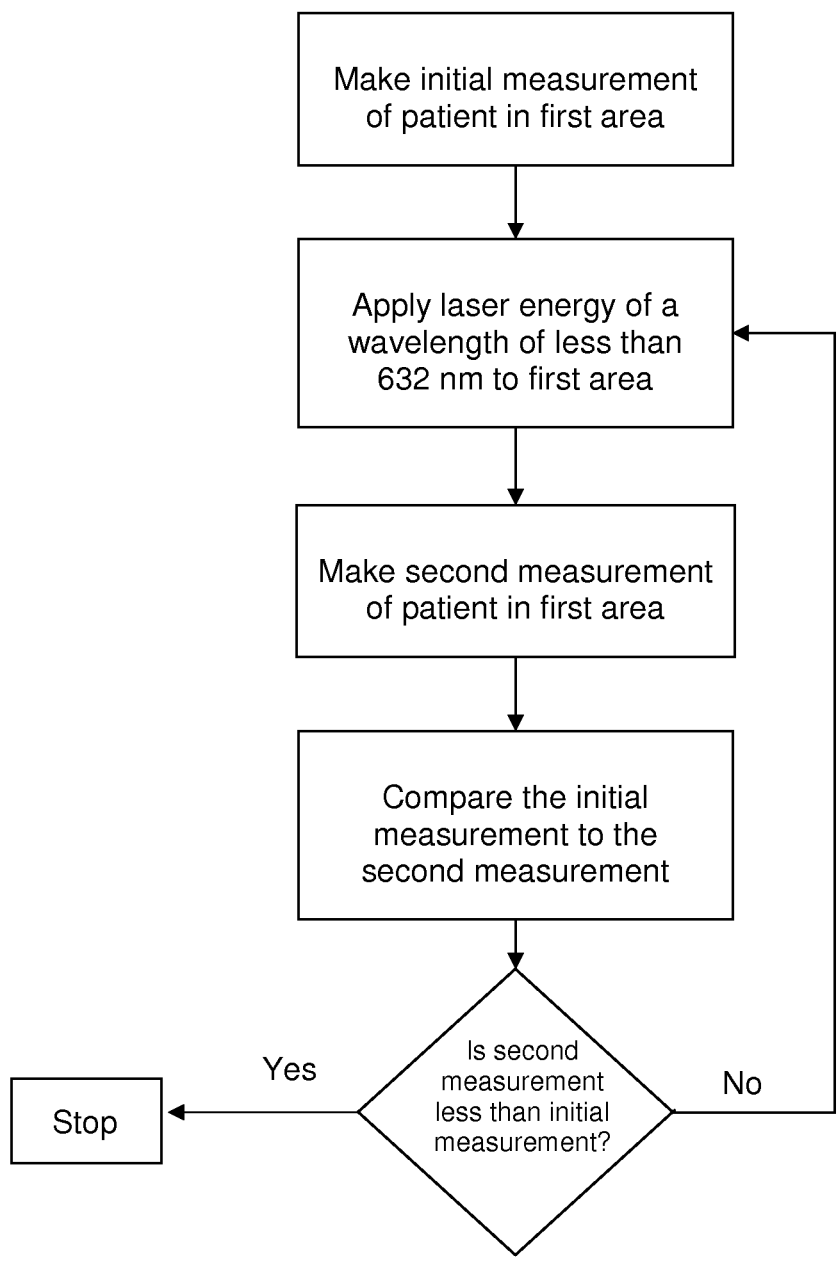
FIG. 2 Flow diagram of present method.
Figure 3:
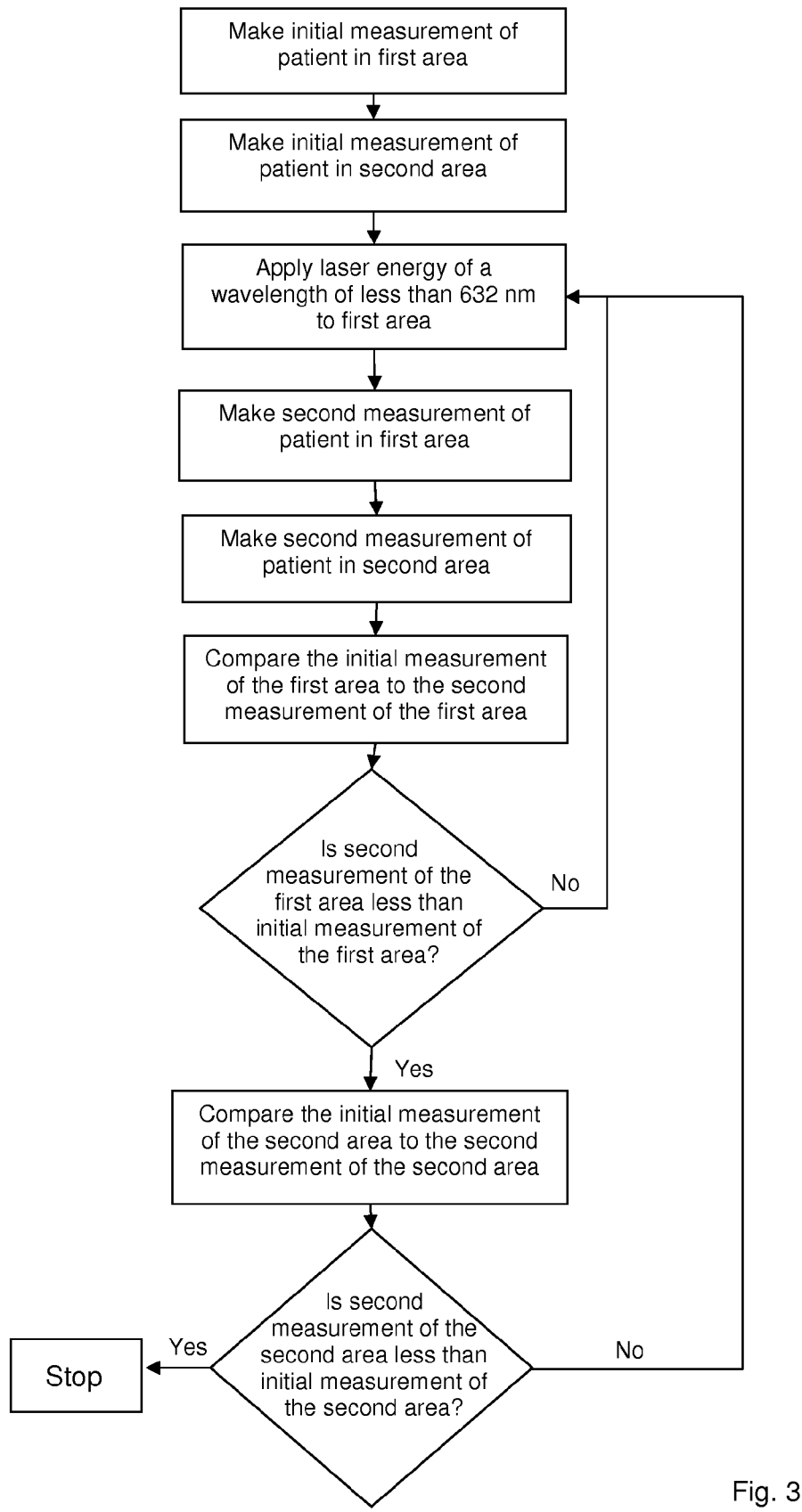
FIG. 3 Flow diagram of alternate embodiment of present method.

In the method's simplest form, a patient's body is measured initially, laser therapy is applied to the patient, and the measurement is repeated shortly after laser treatment to determine whether the measurement is reduced. See FIGS. 1-3. If so, no more laser therapy is applied. If not, more laser therapy is applied until the measurement is reduced. Preferably the same person makes the same measurement before and after treatment, with the same measuring tool, so that measurement variations due to different people and tools are minimized. More specifically, after measurement sufficient laser energy is applied to one or more of areas to cause a reduction in the measurement in the lasered areas. The preferred embodiments use laser light at about 532 nm, 440 nm, or 405 nm with 18 mW or 25 mW laser diodes, applied for 15 minutes, resulting in the application of laser energy at 0.03-0.1 J/cm$^2$. Treatments are repeated, preferably every other day for 1-4 weeks, depending on the amount of slimming desired.

Measurements are made using objective, non-invasive modes to determine the patient's external dimensions, fat mass, or body mass (weight). Tape measures, as exemplified above, are typically used to measure circumference. DEXA, or dual energy x-ray absorptiometry, can be used to determine body fat percentage, fat mass, bone mass and lean mass separately for the arms, trunk, and legs. Ultrasound or magnetic resonance imaging ("MRI") can also be used to measure body fat percentage. Scales can be used to measure weight, hydrostatically or out of the water. Combinations of these measurement modes can be used together to better quantify the slimming.

Figure 1:
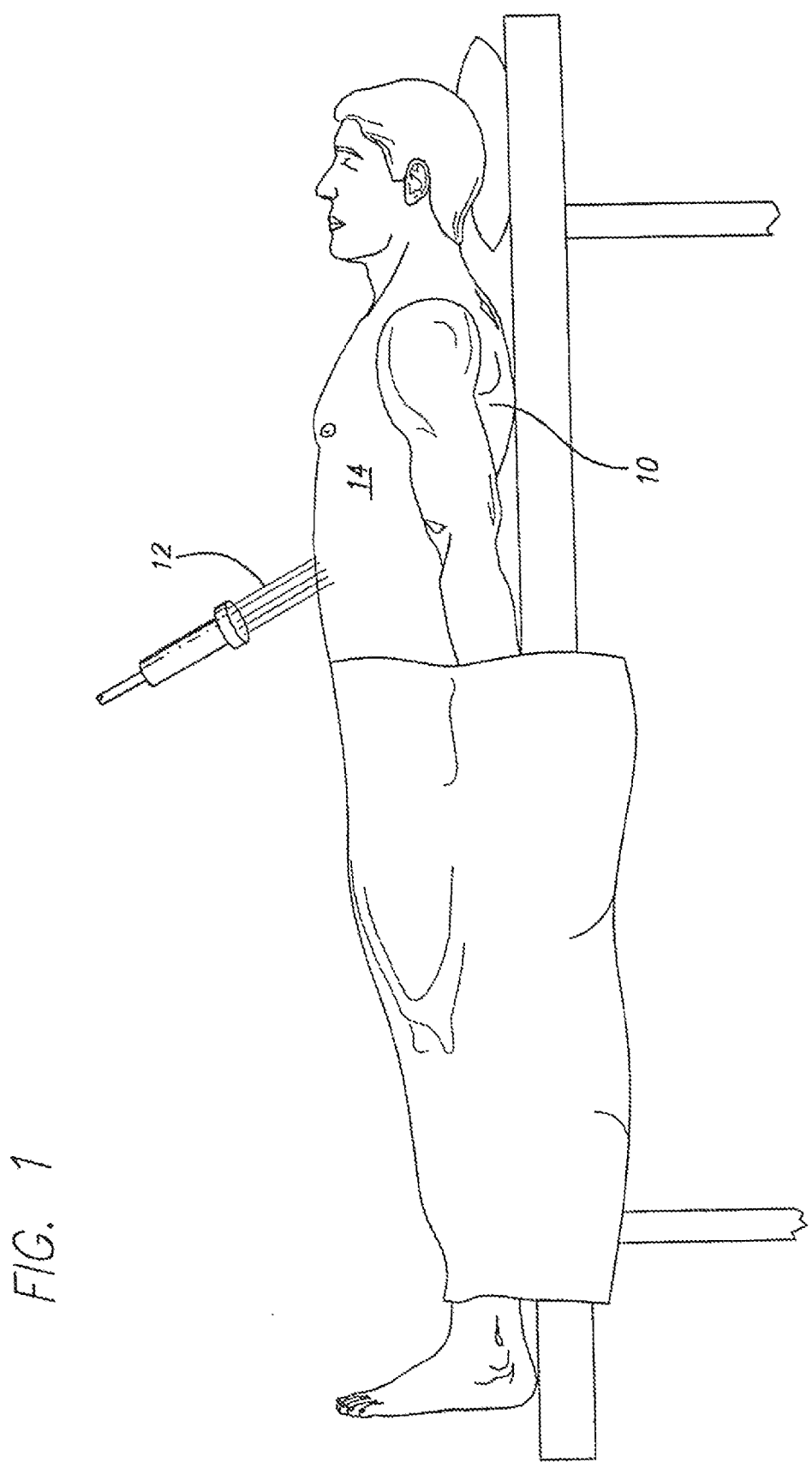
FIG. 1 Schematic illustration of application of low-level laser radiation.

Using external dimension as the measurement mode in a first example, an initial measurement is made of the circumference of one or more areas of a patient's body, preferably the more fatty regions, such as the abdominal, buttock, lower back, thigh, breast or arm regions. For example, a tape measure is used to measure the circumference of the patient's torso at the navel. As illustrated in FIG. 1, laser energy 12 of a wavelength less than about 632 nm is applied to the patient 10 at and around the navel. Sufficient laser energy is applied to the patient to cause the torso measurement to be reduced, typically about 0.03-0.1 J/cm$^2$. The area treated is roughly about 200 cm$^2$-450 cm$^2$ area, or about a 6"×6" to about an 8"×8" square.

A second measurement is taken shortly, preferably within 2 minutes, after the laser treatment to measure the circumference of the patient around the same area of the torso, namely at the navel. If the second measurement is less than the initial measurement then no more laser treatments are made. If, however, the second measurement is not less than the initial measurement, more laser energy of a wavelength less than about 632 nm is applied to the patient at and around the navel, again about 0.03-0.1 J/cm$^2$. A third measurement is taken shortly after the second laser treatment to measure the circumference of the patient's torso at the navel. If the third measurement is less than the initial measurement of the circumference of the patient's torso at the navel, then no more laser treatments are made. If the third measurement is not less than the initial measurement, the process is repeated until the measurement is less than the initial measurement.

Preferably additional measurements are made before and after treatment in other regions of a patient's body, such as the neck, buttock, lower back, thigh, bust, calf, knee, wrist, ankle, or upper arm. These measurements show the slimming effect in areas other than the treated areas and can be used to determine the amount of laser energy applied. Again using external dimensions for example, a tape measure is used to measure the circumference of the patient's torso at the navel and the circumference of the patient's neck, collectively referred to as the initial set of measurements. Laser energy of a wavelength less than about 632 nm is applied to the patient at and around the navel. Sufficient laser energy is applied to the patient to cause the torso measurement to be reduced, typically about 0.03-0.1 J/cm$^2$. A second set of measurements is taken again shortly after the laser treatment, around the patient's torso at and around the patient's neck. If both the second measurement of the patient's torso and the second measurement of the patient's neck are less than those measurements in the initial set of measurements, then no more laser treatments are made. If, however, one or both of the second measurements of the torso and neck is not less than the initial measurement of the torso and neck, more laser energy of a wavelength less than about 632 nm is applied to the patient at and around the navel, again about 0.03-0.1 J/cm$^2$. A third set of measurements is taken shortly after the second application of laser treatment and if both the third measurement of the patient's torso and the third measurement of the patient's neck are less than the initial set of measurements then no more laser treatments are made. If the third set of measurements is not less than the initial set of measurements, the process can be repeated until the torso and neck measurements are less than when first measured. In this manner, treatment with sufficient laser energy applied to one area causes size reduction in the lasered areas, as well as in other areas that were not treated, resulting in overall body slimming.

In yet another embodiment, a patient is treated with laser energy in two areas and overall body slimming is seen. Using the percentage body fat, DEXA is used to measure the patient's initial percentage body fat. Measurements may also be taken of the circumference of the patient's neck and each of the patient's thighs using a tape measure. Laser energy of a wavelength less than about 632 nm is applied to the patient on both thighs and both hips. Sufficient laser energy is applied to the patient to cause the percentage body fat to be reduced, typically about 0.03-0.1 J/cm$^2$. A second set of measurements is taken again shortly after the laser treatment, using DEXA to measure the patient's percentage body fat and a tape measure to measure the circumference around the patient's neck and each of the patient's thighs. If the second measurement of the patient's body fat percentage is less than the initial measurement then overall slimming is achieved and no more laser treatments need to be made. If, however, the body fat percentage is less than initially measured but the external dimensions are not, the patient may be treated again with laser energy to achieve additional overall slimming. In that case, a third set of measurements is taken shortly after the second application of laser treatment and if the patient's external dimensions are less than the initial set of measurements then no more laser treatments are made. If the third set of measurements of external dimensions is not less than the initial set of measurements, the process can be repeated until the thigh and neck measurements are less than when first measured. In this manner, treatment with sufficient laser energy applied to two areas causes size reduction in the lasered areas, as well as in other areas that were not treated, resulting in overall body slimming.

Often patients are satisfied with the slimming results in one therapy session, however each patient may also be subjected to multiple sessions over several weeks' time. Preferably laser energy is applied at about 0.03-0.1 J/cm$^2$ for 15 minutes, every other day for 1-4 weeks, depending on the amount of slimming desired.

Wavelengths shorter than 632 nm are used in the method described herein. The preferred embodiments use laser light at about 532 nm, 440 nm, or 405 nm. A laser device that provides low-level energy is known in the art as a cold laser, such as the inventions described in U.S. Pat. No. 6,013,096 issued to Tucek and U.S. Pat. No. 6,746,473, issued to Tucek and Shanks. These devices use semiconductor diode lasers which are available commercially in a broad range of wavelengths between 405-1500 nm. The laser device may have one or more laser energy sources. Different therapy regimens require diodes of different wattages. The preferred laser diodes employ less than one watt of power, preferably between 10 mW and 50 mW, and most preferably 18 mW or 25 mW diodes. The 18 mW diodes are typically used for patients with body mass index of 20-30, whereas the 25 mW diodes are use for patient having BMI over 30. Diodes of various other wattages may also be employed to achieve the desired laser energy for the given regimen.

The dosage of laser energy required to achieve slimming will vary depending on the thickness of the patient's skin, thickness of fatty tissue, and other biological factors peculiar to each patient. While a person skilled in the art will be able to determine the amount of energy needed to slim the patient by comparing initial and subsequent measurements, applied energy can also be determined by the applied fluence. Preferably a fluence of about 0.03-0.1 J/cm$^2$ is applied each treatment to the targeted area. The following examples are illustrative:

EXAMPLE 1

A patient's waist was measured using a tape measure. The waist measured 100.9 cm in circumference. A 532 nm semiconductor diode laser with maximum power of 18 mW was used to apply laser light to a patient's pad of fat located on his belly of about 400 cm$^2$. The laser energy was applied for 15 minutes in a back-and-forth sweeping motion across the fat area without touching the patient, applying about 16.2 J of laser energy. The patient's waist was measured again using the same tape measure. The waist measured 99.7 cm in circumference. The treatment was repeated again once a week for 4 more weeks. This non-invasive procedure produced the same amount of slimming in the targeted area as would be seen with treatment using red laser light for 20 minutes every day for two weeks, but had an additional benefit of slimming the patient's body overall. The patient suffered no pain or bruising.

EXAMPLE 2

A patient's thigh was measured using a tape measure. The thigh measured 62.5 cm in circumference. A 532 nm semiconductor diode laser with maximum power of 25 mW was used to apply laser light to an area of the patient's thigh of about 400 cm$^2$. The laser energy was applied for 15 minutes in a back-and-forth sweeping motion across the fat area without touching the patient, applying about 22.5 J of laser energy. The patient's thigh was measured again using the same tape measure. The waist measured 61.5 cm in circumference and showed a decrease in visible cellulite. The treatment was repeated again every other day for 4 more weeks. This non-invasive procedure produced the same amount of slimming in the targeted area as would be seen with treatment using red laser light for 20 minutes every day for two weeks. The patient suffered no pain or bruising.

EXAMPLE 3

A patient's waist and neck were measured using a tape measure. The waist measured 100.9 cm in circumference and the neck measured 43.2 cm. A 440 nm semiconductor diode laser with maximum power of 25 mW was used to apply laser light to a patient's pad of fat located on his belly of about 232 cm$^2$. The laser energy was applied for 15 minutes in a back-and-forth sweeping motion across the fat area without touching the patient, applying about 22.5 J of laser energy. The patient's waist and neck were measured again using the same tape measure. The waist measured 99.7 cm in circumference and the neck 42.5 cm. The treatment was repeated daily for the first week and every other day for the next week. This non-invasive procedure produced the same amount of fat reduction as would be seen with treatment using red laser light for 20 minutes every day for two weeks. The patient suffered no pain or bruising.

EXAMPLE 4

A patient's body fat percentage was determined using a DEXA scan. The patient's body fat was 32.0%. A 405 nm semiconductor diode laser with maximum power of 18 mW was used to apply laser light to a patient's pad of fat located on his lower back of about 400 cm$^2$. The laser energy was applied for 15 minutes in a back-and-forth sweeping motion across the fat area without touching the patient, applying about 16.2 J of laser energy. The patient's body fat percentage was re-measured using a DEXA scan and found to be 30.0%. A similar amount of laser energy was applied every other day for 3 more weeks. The final measurement was 28% body fat. This non-invasive procedure produced the same amount of fat reduction as would be seen with treatment using red laser light for 20 minutes every day for two weeks. The patient suffered no pain or bruising.

While there has been illustrated and described what is at present considered to be a preferred embodiment of the present invention, it will be understood by those skilled in the art that various changes and modifications may be made, and equivalents may be substituted for elements thereof without departing from the true scope of the invention. Therefore, it is intended that this invention not be limited to the particular embodiment disclosed as the best mode contemplated for carrying out the invention, but that the invention will include all embodiments falling within the scope of the appended claims.

We claim:

1. A method of slimming a patient, the method comprising applying monochromatic laser energy having a wavelength shorter than 570 nm externally to the patient at a targeted area in a dose rate that causes no detectable temperature rise of the treated tissue.

2. The method according to claim 1 wherein the laser energy is monochromatic green.

3. The method according to claim 1 wherein the laser energy is about 532 nm.

4. The method according to claim 1 wherein the laser energy is monochromatic violet.

5. The method according to claim 1 wherein the laser energy is about 440 nm.

6. The method according to claim 1 wherein the laser energy is about 405 nm.

7. The method according to claim 1 wherein applying laser energy to the targeted area of the patient's body comprises using an 18 mW laser diode to apply laser energy at 0.03-0.1 J/cm$^2$ for 15 minutes, every other day for 1-4 weeks.

8. The method according to claim 1 wherein applying laser energy to the targeted area of the patient's body comprises using an 25 mW laser diode to apply laser energy at 0.03-0.1 J/cm$^2$ for 15 minutes, every other day for 1-4 weeks.

9. A method of slimming a patient, the method comprising applying unfiltered laser energy having a wavelength shorter than 570 externally to the patient at a first area in a dose rate that causes no detectable temperature rise of the treated tissue.

10. The method according to claim 9 wherein the laser energy is green.

11. The method according to claim 9 wherein the laser energy is about 532 nm.

12. The method according to claim 9 wherein the laser energy is violet.

13. The method according to claim 9 wherein the laser energy is about 440 nm.

14. The method according to claim 9 wherein the laser energy is about 405 nm.

15. The method according to claim 9 wherein applying laser energy to the targeted area of the patient's body comprises using an 18 mW laser diode to apply laser energy at 0.03-0.1 J/cm$^2$ for 15 minutes, every other day for 1-4 weeks.

16. The method according to claim 9 wherein applying laser energy to the targeted area of the patient's body comprises using an 25 mW laser diode to apply laser energy at 0.03-0.1 J/cm$^2$ for 15 minutes, every other day for 1-4 weeks.

* * * * *